(12) United States Patent
Moulin

(10) Patent No.: US 6,488,027 B1
(45) Date of Patent: Dec. 3, 2002

(54) POWDER INHALER

(75) Inventor: Claude Moulin, Sion (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/657,967

(22) Filed: Sep. 8, 2000

Related U.S. Application Data

(63) Continuation of application No. PCT/EP99/01487, filed on Mar. 8, 1999.

(30) Foreign Application Priority Data

Mar. 10, 1998 (GB) .............................. 9805102

(51) Int. Cl.$^7$ ............................................ A61M 16/00
(52) U.S. Cl. ............................ 128/203.21; 128/203.15; 128/203.12
(58) Field of Search ................... 128/203.12, 203.15, 128/203.21, 205.21; 604/58

(56) References Cited

U.S. PATENT DOCUMENTS

| | | | |
|---|---|---|---|
| 2,814,296 A | 11/1957 | Everett et al. | 128/339 |
| 3,071,856 A | 1/1963 | Fischbein | 30/346 |
| 3,203,829 A | 8/1965 | Seyer et al. | 117/132 |
| 3,209,754 A | 10/1965 | Brown | 128/337 |
| 3,379,552 A | 4/1968 | Kurtz et al. | 117/7 |
| 3,518,110 A | 6/1970 | Fischbein et al. | 117/93.4 |
| 3,652,342 A | 3/1972 | Fischbein et al. | 148/6.35 |
| 3,700,489 A | 10/1972 | Borysko | 117/106 |
| 3,838,512 A | 10/1974 | Sanderson | 30/346.54 |
| 3,942,532 A | 3/1976 | Hunter et al. | 128/335.5 |
| 3,949,751 A | 4/1976 | Birch et al. | |
| 3,958,570 A * | 5/1976 | Vogelman et al. | 128/218 DA |
| 3,991,761 A | 11/1976 | Cocozza | |
| 4,012,551 A | 3/1977 | Bogaty et al. | 428/192 |
| 4,275,813 A | 6/1981 | Noiles | 206/339 |
| 4,307,984 A * | 12/1981 | Patterson | 408/145 |
| 4,621,026 A * | 11/1986 | Robinson | |
| 5,197,962 A * | 3/1993 | Sansom et al. | 606/45 |
| 5,266,359 A * | 11/1993 | Spielvogel | 427/388.4 |
| 5,352,378 A | 10/1994 | Mathisen et al. | |
| 5,685,294 A | 11/1997 | Gupte et al. | |
| 5,685,961 A | 11/1997 | Pourrezaei et al. | |
| 5,743,251 A * | 4/1998 | Howell et al. | 128/200.14 |
| 5,919,172 A * | 7/1999 | Golba, Jr. | 604/272 |
| 5,985,355 A * | 11/1999 | Walther et al. | 427/2.28 |
| 6,015,398 A * | 1/2000 | Arimatsu et al. | 604/272 |
| 6,026,809 A * | 2/2000 | Abrams et al. | 128/203.15 |
| 6,159,233 A * | 12/2000 | Matsuzawa | 606/223 |
| 6,298,256 B1 * | 10/2001 | Meyer | 600/373 |

FOREIGN PATENT DOCUMENTS

| | | | |
|---|---|---|---|
| DE | 39 27 170 | 2/1991 | |
| EP | 0 092 383 A2 | 10/1983 | A61B/17/08 |
| EP | 0 528 764 B1 | 2/1993 | |
| EP | 0 528 764 A1 | 2/1993 | |
| GB | 1485163 | 9/1977 | A61M/15/00 |
| GB | 2052431 | 1/1981 | B65D/69/00 |
| WO | WO 83/02124 | 6/1983 | C25D/5/00 |
| WO | WO 96/26751 | 9/1996 | A61M/5/00 |

OTHER PUBLICATIONS

Int. J. of Materials and Product Technology, vol. 1, No. 2, 1986, pp. 290–300.

Brochure from Argos Electroless Nickel Plating.

March, "Response to Question Concerning PTFE Coatings on Surgical Staples", The Industrial Unit of Tribology, pp. 1–6 (1992).

Roberto, "Electroless Nickel/PTFE Composite Coatings", Products Finishing (Cincinnati), vol. 53, No. 7, pp. 46–49 (1989).

Products Finishing (London), vol. 39, No. 11, pp. 11–12 (1986).

"Dental Micro–Cutter of Good Efficiency –Has Surface Coated with Crystals of Diamond Like Carbon, with Gaps Filled by Electroless Nickel Coating" (1991) –Abstract 91–078323/11 KANE.

Jeanmenne et al., "*Electroless* *Plating* on Medical *Catheters*", Product Finishing (Cincinnati), vol. 61, No. 11, pp. 60–62, 64 and 66–67 (1997) –Abstract 1997:555176 HCAPLUS.

Prasad, "Coating Surgical Needles with Lubricant Soln –by Feeding Them Between Opposed Endless Belts Rotated in Opposite Directions and Whose Outer Surfaces Have Been Wetted with Lubricant Soln", American Cyanamid Co. (1996) –Abstract 96–341460/34 Derwent.

Prasad et al., "Silicone Coating Compsns –Useful for Lubrication of e.g. Hypodermic Needles or Razor Blades", American Cyanamid Co. (1994) –Abstract 95–008059/02 Derwent.

Thomas et al., "Nonflammable Compsn. for Lubricating Medical Articles –Comprising Silicone Lubricant, Highly Fluorinated Organic Cpd. and Fluorine–Free Solvent", Minnesota Mining & Mfg. Co. (1994) –Abstract 94–316113/39 Derwent.

"Attaching Suture to Unbored Surgical Needle –with Shrunk–on Plastic Tube after Coating Lubricant on Suture Tip to Reduce Pull Out Force", US Surgical Corp. (1993) –Abstract 93–367746/46 Derwent.

Granger et al., "Mfr. of Siliconised Surgical Needles –with a Coating of a Cured Aminoalkyl Siloxane", US Surgical Corp. (1992) –Abstract 92–235717/29 KANE.

(List continued on next page.)

Primary Examiner—John G. Weiss
Assistant Examiner—Mital Patel
(74) Attorney, Agent, or Firm—John D. Thallemer; E. Jay Wilusz

(57) ABSTRACT

This invention relates to single dose dry powder inhalers in which medicament is stored in a capsule and is released by piercing the capsule wall with polymer-coated steel pins. Methods of preparation of polymer-coated piercing means and their use in releasing the medicament from the capsule are described.

11 Claims, No Drawings

OTHER PUBLICATIONS

Williamitis et al., "Articles with Metal Surface Coated with Non–Curing Lubricant –Comprising Polysiloxane Substd. by Polar Gp.", Becton Dickinson Co. (1992) –Abstract 92–209699/26 Derwent.

"Surgical Instrument for Haemostatic Cutting of Tissue – Comprising a Heated Blade with an Adherent Coating to Reduce Tissue Accumulation", SHAW, 9 pages, Drawing No., 1a/6 –Abstract (Image) 89–262807 [36] Derwent.

Niedospial et al., "Cartridge Needle Assembly for Medicaments with Lubricated Seal and Cap–Reduces Frictional Forces of Needle Insertion and Prevents Blockage, or Debris Injection into Patient from Resilient Seal and Silicone Lubricants by Means of PTFE Application", Sanofi Winthrop Inc., Drawing No. 6/7 –Abstract (Image) 96–425106 [42] Derwent.

Hu et al., "The Effects of Molecular Weight and Crystallinity on Wear of Polytetrafluoroethylene", pp. 636–642.

Clauss, "Solid Lubricants and Self–Lubricating Solids", Chapter 9, Fluorocarbons, Academic Press, p. 195 (1972).

Industrial Tribology, Tribology Series 8, "The Practical Aspects of Friction, Lubrication and Wear", Jones and Scott, Eds., Elsevier Scientific Publishing Company, Amsterdam, The Netherlands (1983).

Dowson, "History of Tribology", Section 11.14 (Bio–tribology), Longman Group Limited, p. 485 (1979).

Briscoe et al., "The Influence of γ–Irradiation Upon the Friction and Wear of PTFE", pp. 643–649.

Homsy et al., "Reduction of Tissue and Bone Adhesion to Cobalt Alloy Fixation Appliances", J. Biomed. Mater Res., vol. 6, pp. 451–464 (1972).

Bowers et al., "Frictional Behavior of Polyethylene, Polytetrafluoroethylene & Halogenated Derivatives", Lubrication Engineering, pp. 204–208 and 218–219 (1953).

Robinson, "Wear and Friction Resistant Coating for Metal – Prepd. by Thermally Diffusing Soft Meal or Organic Lubricant into Porous Plating" –Abstract 83–711631 [28] Derwent.

Roberto, "Electroless *Nickel*/*PTFE* Composite * Coatings*", Products Finishing (Cincinnati), vol. 53, No. 7, pp. 46–49 (1989) –Abstract EI8909087411 Compendex.

Daniels et al., "Effect of **Coating* of Injection Molding Tools on the Mold Release Force", Metalloberflaeche, vol. 43, No. 2, pp. 55–57 (1989) –Abstract (German) EI8910106699 Compendex.

Ebdon, "Electroless *Nickel* /P.T.F.E. Composites – The Niflor Process", Int. J. Mater. Prod. Technol., vol. 1, No. 2, pp. 290–300 (1986) –Abstract EI8712125462 Compendex.

Ebdon, "Niflor Process –A Growth Phenomenon", Product Finishing (London), vol. 39, No. 11, pp. 8 and 11–12 (1986) –Abstract EI870908615 Compendex.

Tulsi, "Composite *PTFE*–*Nickel* *Coatings* for *Low* *Friction* Applications", Inst. of Metal Finishing, Birmingham, England, 21 pages (1983) –Abstract EIM8506–032808 Compendex.

Pourrezaei et al., "Method for Fabrication of Metalized Medical Devices", P&D Medical Coatings, Inc., 18 pages (1997) –Abstract 1997:735814 HCAPLUS.

Ebdon, "Book Reviews. 'Niflor' –A New Generation Approach to Self–Lubricating Surfaces", Materials & Designs, vol. 6, No. 1, pp. 33–36 (1985) –Abstract Pascal 85–0202391.

Du Pont Specialty Chemicals, Dyes and Chemicals Division, Information Bulletin, "Vydax® –Fluorotelomer Dispersions", Du Pont publication, Bulletin V–3, pp. 1–11 (1979).

Pacesetter, "Vydax® –Celebrating 25 Years of Outstanding Performance", Du Pont, 4 pages (1998).

Du Pont Petroleum Chemicals, 'Vydax® 1000 –Fluorotelomer Disperson, Du Pont, Bulletin Y–1, pp. 1–8.

International Search Report PCT/EP99/01487 (1999).

* cited by examiner

POWDER INHALER

This is a continuation of International Application No. PCT/EP99/01487, filed on Mar. 8, 1999.

This invention relates to single dose dry powder inhalers in which medicament is stored in a capsule prior to release.

It is well-known to pierce capsules with a metal pin or other cutting means in an inhaler. Capsule-cutting means are disclosed for example in DE 39 27 170 and in EP 528 764.

An inhaler for powdered medicaments is described in U.S. Pat. No. 3,991,761 (hereafter referred to as Inhaler A). Inhaler A comprises a recess for receiving a capsule, and push buttons are provided which carry sharpened metal pins and are held in position by biasing springs. In use the capsule is pierced by the spring-loaded pins and on release of the push buttons, the pins retract from the perforated capsule allowing medicament to pass out therefrom.

A problem encountered with known capsule-piercing mechanisms is that the cutting means, e.g. metal pin, can become adhered to a capsule wall. This prevents complete release of medicament for inhalation and causes frustration amongst users.

The present applicants have sought to overcome this problem, and have found that a polymer coating applied to the metal pins permits complete release after capsule-puncture.

In one aspect, therefore, this invention provides an inhaler comprising metal capsule-piercing means which is coated with a polymer.

In another aspect this invention provides the use of polymer-coated metal capsule-piercing means in an inhaler for faster, more complete and effective release of a medicament.

In accordance with the present invention, piercing means are provided that may have at least one coating of an inert polymer characterized by (i) excellent antiadhesive properties, i.e. highly lubricating, properties, for example a polymer having a low friction coefficient, e.g. a friction coefficient (which is defined as the dimensionless quotient obtained by dividing the value of the force necessary to move one body over another at a constant speed by the weight of the body) of at least 0.1 under light loads and (ii) high thermal and chemical inertness. Preferred polymers include any inert polymer, for example fluorocarbon polymers containing —$CF_2$—$CF_2$— units, including copolymers thereof, having different terminal groups at the polymer chain ends, for example hydrogen, a halogen, a halogenated carbon, e.g. trichlorocarbon, a carboxylic acid, an alkylgroup, or an alcohol, depending on the method of producing the polymer. Especially preferred is polytetrafluoroethylene (PTFE) also known as TEFLON®. The molecular weights of the polymers used for coating the piercing means may range from about $2 \times 10^3$ to about $2 \times 10^6$ Daltons. Preferably, these polymers are incorporated homogeneously, e.g. uniformly distributed, for example in an alloy matrix, at a concentration of up to 30%, e.g. from 5 to 30%. These alloys may contain chromium and/or one or more elements of Group VIII of the Periodic Table, for example iron, cobalt, nickel, preferably nickel, and/or a noble metal, for example ruthenium, rhodium, palladium. Particularly preferred are nickel phosphorous alloys which preferably contain about 90 to 93% by weight nickel and about 7 to 10% by weight phosphorous.

Coterminous piercing of the capsule may be achieved by one or more pins at each end of the capsule. The coating or coatings may cover at least the portion of a pin or pins which come in contact and pierce the capsule, but preferably they cover the whole surface of the pin or pins. More than one alloy may be used to apply more than one coating to the pins, particularly preferred are two coatings. The polymer coating or coatings may typically have a total thickness of between about 1 to about 30 microns, for example a first coating may have a thickness of about 5 to about 15 microns, and a second coating may have a thickness of about 3 to 10 microns.

Thus, in one embodiment of this invention, piercing means may be coated with PTFE or an alloy matrix, e.g. a chromium or a nickel phosphorous alloy, or an alloy matrix containing PTFE particles, e.g. a PTFE-containing nickel phosphorous alloy, also known as CHENIFLON™.

In a particularly preferred embodiment of this invention, steel pins, e.g. stainless steel pins, for use in an inhalation device are coated with a first layer of a nickel phosphorous alloy, e.g. NIPLOY™, to a thickness of between about 5 and about 15 microns and a second layer containing about 20 to 30% by volume PTFE particles homogeneously incorporated in a nickel phosphorous alloy matrix may be applied at a thickness of between 3 and 10 microns onto the first layer.

Preferably, the composition of a plated deposit contains about 80 to 95%, e.g. 85% by weight nickel, 5 to 20%, e.g. 6.6% by weight phosphorous and up to 30%, e.g. 8.4% by weight PTFE. The PTFE content in a composite of 8.4% by weight may correspond to approximately 25% by volume in the deposit.

Polymers may be applied to the pins, e.g. steel pins, using techniques suitable to give a uniform coating. Typically, conventional coating techniques include (i) applying the polymers in form of a, preferably fine, dispersion and (ii) evaporating the liquid medium to form the coating. Such techniques include for example (i) dipping the pins into a dispersion of an alloy and controlling the coating thickness by polymer concentration, rate of dipping and withdrawing, and number of applications;

(ii) wiping or brushing dilute alloy dispersions onto pin surfaces, particularly useful for partial surface coating;

(iii) spraying, for example air spraying of an alloy dispersed in a less volatile solvent using conventional spray equipment, airless spraying using dilute alloy dispersions, or electrostatic spraying;

(iv) depositing a coating using aerosol formulations;

(v) by ultraviolet photopolymerization;

(vi) by RF sputtering; or (vii) by electrophoresis of such a dispersion onto the pins.

Suitable liquid media to form a dispersion include aqueous solutions, freons, for example dichlorodifluoromethane, dichlorotetrafluoroethane, and the like, including mixtures of these media. The dispersion may be preferably fine such that the particles remain uniformly distributed through the solution with little or no agitation. However, most preferably the polymer coatings are formed by depositing a coating using plating processes, particularly preferred is an electroless nickel composite coating process.

Typically, in an electroless nickel plating process direct reduction of the nickel onto the surface takes place in solution in the presence of reducing agents which provide the necessary energy, e.g. sodium hypophosphite, boron compounds or hydrazine. Most preferably the reduction reaction is fueled by hypophosphite, which results in co-deposition of small amounts of phosphorous, e.g. up to 10%, e.g. from about 7 to 10% by weight. A corresponding composite process further includes particles in the plating solution, for example polymers, e.g. PTFE. Typically a chemical composition of a plating solution may contain 6 g/l nickel metal, 30 g/l sodium hypophosphite, 3–6 g/l PTFE powder, 10–30 g/l organic acids, and stabilizers in picomolar concentrations. Typical operating conditions may include a pH of about 4.7 to 5.0 and a temperature of about 183 to 193 F.

Thus, in a particularly preferred embodiment a coating may be applied by electroless nickel plating or composite coating, e.g. using the Cheniflon™ process from the Argos company of Italy.

The following non-limiting examples were carried out to illustrate the processes of the present invention:

TEST 1

50 Beclometason 400 Cyclocaps® are used successively in Inhaler A with uncoated steel pins at 20° C. After perforation of each capsule the push buttons are released and it is observed that the pins are retained in, or incompletely withdrawn from, 15 capsules.

This is repeated with inhaler A with Niploy™ and Cheniflon™ coated steel pins and no pin retention is observed in any capsule.

TEST 2

50 Salbutanol 200 Cyclocaps® are used successively in Inhaler A with uncoated pins at 20° C. After perforation of each capsule the push buttons are released and the pins are retained in, or incompletely withdrawn from, 18 capsules.

This is repeated with inhaler A with Niploy™ and Cheniflon™ coated pins and no pin retention by any capsule is observed.

What is claimed is:

1. An inhaler device comprising a steel capsule-piercing means for piercing a capsule, wherein at least a portion of said steel capsule piercing means which comes in contact with and pierces the capsule, is coated with
    (1) an alloy layer wherein the alloy comprises at least one metal selected from the group consisting of chromium, Group VIII metal, and the noble metal; and
    (2) an alloy matrix layer wherein the alloy matrix comprises (i) inert polymer particles, and (ii) an alloy comprising at least one metal selected from the group consisting of chromium, Group VIII metal, and noble metal.

2. The inhaler device according to claim 1 wherein the metal is selected from the group consisting of iron, cobalt, nickel, ruthenium, rhodium, palladium, and combinations thereof.

3. The inhaler device according to claim 2 wherein the metal is nickel.

4. The inhaler device according to claim 1 wherein the alloy matrix additionally comprises phosphorus.

5. The inhaler device according to claim 4, wherein the alloy comprises nickel and phosphorus.

6. The inhaler device according to claim 5 wherein the alloy comprises 90 to 93 weight percent nickel and 7 to 10 weight percent phosphorous, based on the total weight of the alloy.

7. The inhaler device according to claim 1 wherein the polymer is a fluorocarbon polymer.

8. The inhaler device according to claim 7 wherein the polymer is polytetrafluoroethylene.

9. The inhaler device according to claim 1 wherein the steel capsule piercing means is coated with (1) an alloy layer comprising nickel and phosphorous, and (2) an alloy matrix layer comprising nickel, phosphorous, and particles of polytetrafloroethylene.

10. The inhaler device according to claim 1 wherein the alloy layer has a thickness of from about 5 to about 15 microns and the alloy matrix layer has a thickness of 3 to 10 microns.

11. The inhaler device according to claim 1 wherein the alloy matrix layer contains 20 to 30% by volume polytetrafluoroethylene.

* * * * *